US012560605B2

(12) United States Patent
Rotkin et al.

(10) Patent No.: US 12,560,605 B2
(45) Date of Patent: Feb. 24, 2026

(54) METHODS AND SYSTEMS FOR EARLY DETECTION OF VIRAL DISEASES

(71) Applicants: The Penn State Research Foundation, University Park, PA (US); The National Institute of Standards and Technology, Rockville, MD (US); University of North Carolina at Greensboro, Greensboro, NC (US)

(72) Inventors: Vyacheslav V. Rotkin, State College, PA (US); Ming Zheng, Rockville, MD (US); Tetyana Ignatova, Whitsett, NC (US); Daniel Hayes, University Park, PA (US); Suresh Kuchipudi, State College, PA (US)

(73) Assignees: THE PENN STATE RESEARCH FOUNDATION, University Park, PA (US); GOVERNMENT OF THE UNITED STATES OF AMERICA, AS REPRESENTED BY THE SECRETARY OF COMMERCE, Gaithersburg, MD (US); UNIVERSITY OF NORTH CAROLINA AT GREENSBORO, Greensboro, NC (US)

( * ) Notice: Subject to any disclaimer, the term of this patent is extended or adjusted under 35 U.S.C. 154(b) by 530 days.

(21) Appl. No.: 17/327,151

(22) Filed: May 21, 2021

(65) Prior Publication Data

US 2021/0364517 A1 Nov. 25, 2021

Related U.S. Application Data

(60) Provisional application No. 63/028,295, filed on May 21, 2020.

(51) Int. Cl.

*G01N 33/569* (2006.01)
*G01N 33/53* (2006.01)
*G01N 33/543* (2006.01)
*G01N 33/58* (2006.01)

(52) U.S. Cl.

CPC ... *G01N 33/56983* (2013.01); *G01N 33/5302* (2013.01); *G01N 33/54326* (2013.01); *G01N 33/582* (2013.01); *G01N 2333/165* (2013.01); *G01N 2333/948* (2013.01)

(58) Field of Classification Search

CPC ......... G01N 33/56983; G01N 33/5302; G01N 33/54326; G01N 33/582; G01N 2333/165; G01N 2333/948

See application file for complete search history.

(56) References Cited

PUBLICATIONS

Xu, Kaijia et al. "A green deep eutectic solvent-based aqueous two-phase system for protein extracting." Analytica chimica acta vol. 864 (2015): 9-20. doi: 10.1016/j.aca.2015.01.026 (Year: 2015).*

(Continued)

*Primary Examiner* — Gregory S Emch
*Assistant Examiner* — Mckenzie A Dunn
(74) *Attorney, Agent, or Firm* — Troutman Pepper Locke LLP

(57) ABSTRACT

The invention is directed to methods and systems for early detection of viral diseases, and more specifically to systems and methods for early detection of viral diseases that are capable of detecting very low viral loads, such as for example and not limitation, SARS-CoV-2 loads.

17 Claims, 1 Drawing Sheet

(56) References Cited

PUBLICATIONS

Jue, Erik et al. "Using an aqueous two-phase polymer-salt system to rapidly concentrate viruses for improving the detection limit of the lateral-flow immunoassay." Biotechnology and bioengineering vol. 111, 12 (2014): 2499-507. doi:10.1002/bit.25316 (Year: 2014).*
Torres-Acosta, Mario A et al. "Aqueous Two-Phase Systems at Large Scale: Challenges and Opportunities." Biotechnology journal vol. 14,1 (2019): e1800117. doi:10.1002/biot.201800117 (Year: 2019).*
Yadav, N. et al., "Synthesis and characterization of hydrothermally synthesized superparamagnetic APTS-ZnFe2O4 nanoparticles: DNA binding studies for exploring biomedical applications". Chem. Pap. 74, 1177-1188 (2020). (Year: 2020).*
Zhang, Xiaoqing et al. "ACE2 and COVID-19 and the resulting ARDS." Postgraduate medical journal vol. 96, 1137 (2020): 403-407. doi:10.1136/postgradmedj-2020-137935 (Year: 2020).*
Toseland, Christopher P. "Fluorescent labeling and modification of proteins." Journal of chemical biology vol. 6,3 85-95. Apr. 13, 2013, doi:10.1007/s12154-013-0094-5 (Year: 2013).*
Al Qaraghuli, Mohammed M et al. "Antibody-protein binding and conformational changes: identifying allosteric signalling pathways to engineer a better effector response." Scientific reports vol. 10,1 13696. Aug. 13, 2020, doi:10.1038/s41598-020-70680-0 (Year: 2020).*
Rabia, Lilia A et al. "Understanding and overcoming trade-offs between antibody affinity, specificity, stability and solubility." Biochemical engineering journal vol. 137 (2018): 365-374. doi:10.1016/j.bej.2018.06.003 (Year: 2018).*
Poosarla, Venkata Giridhar et al. "Computational de novo design of antibodies binding to a peptide with high affinity." Biotechnology and bioengineering vol. 114,6 (2017): 1331-1342. doi:10.1002/bit.26244 (Year: 2017).*
Lloyd, C et al. "Modelling the human immune response: performance of a 1011 human antibody repertoire against a broad panel of therapeutically relevant antigens." Protein engineering, design & selection : PEDS vol. 22,3 (2009): 159-68. doi:10.1093/protein/gzn058 (Year: 2009).*
Khan, Tarique, and Dinakar M Salunke. "Adjustable locks and flexible keys: plasticity of epitope-paratope interactions in germline antibodies." Journal of immunology (Baltimore, Md. : 1950) vol. 192,11 (2014): 5398-405. doi:10.4049/jimmunol.1302143 (Year: 2014).*
Goel, Manisha et al. "Plasticity within the antigen-combining site may manifest as molecular mimicry in the humoral immune response." Journal of immunology (Baltimore, Md. : 1950) vol. 173,12 (2004): 7358-67. doi:10.4049/jimmunol.173.12.7358 (Year: 2004).*
Edwards, Bryan M et al. "The remarkable flexibility of the human antibody repertoire; isolation of over one thousand different antibodies to a single protein, BLyS." Journal of molecular biology vol. 334,1 (2003): 103-18. doi:10.1016/j.jmb.2003.09.054 (Year: 2003).*

* cited by examiner

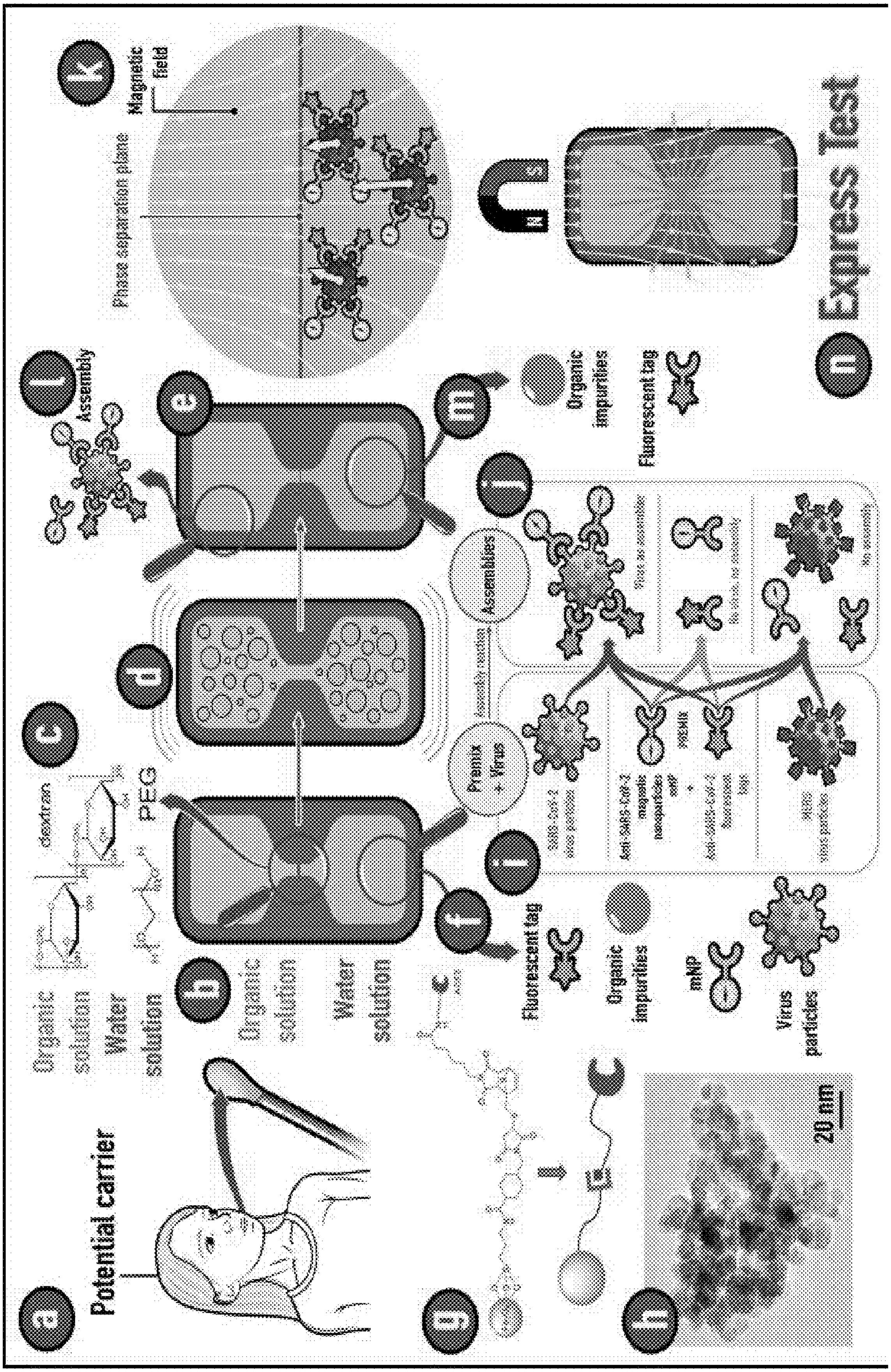
a
Potential carrier
Organic solution
Water solution
dextran
PEG
b
Organic solution
Water solution
c
d
e
f
Fluorescent tag
Organic impurities
mNP
Virus particles
g
h
20 nm
i
Premix + Virus
Assemblies
j
l
Assembly
m
Organic impurities
Fluorescent tag
k
Phase separation plane
Magnetic field
n
Express Test

METHODS AND SYSTEMS FOR EARLY DETECTION OF VIRAL DISEASES

CROSS-REFERENCE TO RELATED APPLICATIONS

This application claims priority to U.S. Provisional Patent Application No. 63/028,295, filed May 21, 2020, the content of which is herein fully incorporated by reference in its entirety.

GOVERNMENT SPONSORSHIP

This invention was made with government support under Hatch Act Project No. PEN04588 awarded by the United States Department of Agriculture. The Government has certain rights in the invention.

BACKGROUND OF THE INVENTION

1. Field of the Invention

Embodiments of the present invention relates generally to methods and systems for early detection of viral diseases, and more specifically to systems and methods for early detection of viral diseases that are capable of detecting very low viral loads, such as for example and not limitation, SARS-CoV-2 loads.

2. Background

The outbreak of SARS-CoV-2 unveiled gaps in the capacity to quickly develop and fabricate tests for a new viral pathogen. Currently there are no simple and reliable methods for an early detection of the virus, during the incubation period or in asymptomatically infected patients who may transmit the virus. Although sensing the living virus at such an early stage is much harder, it is extremely important for preventing the spread of infection. During the COVID-19 outbreak, thousands of potentially infected individuals, being asymptomatic, freely travelled across the borders, contributing to the propagation of a global pandemic disease, and in particular, to the high infection level in US.

For express point-of-care (POC) detection, most of the very sensitive but also expensive and consuming technologies (like PCR and other nucleic acid based or immunosorbent assays, electrochemical and surface plasmon resonance sensing, optical spectroscopy and Raman scattering, to name a few) will not be applicable as they require bulky equipment, trained operators, costly components, or a combination of the above. A new technology, apt for mass production of a POC express tests, must address the following challenges: cost, complexity and time of test for mass diagnostics of patients; limit-of-detection (LoD) and accuracy (low false negatives/positives) for presymptomatic (early) detection at very low virus load; capability to integrate prescreening with more accurate post-screening identification methods (pass positive tests for further inspection).

Among simple methods, fluorescent tag visualization is attractive as it allows detection of the analyte in a single step. However, in order to reach the aim of detection of viral particles in a liquid sample at extremely low concentration the typical fluorescent signal is too weak to detect without special tools. This can be a major barrier for such an early detection technology: both the efficiency of binding of a tag/beacon to the analyte (~signal) and the background fluorescence (~noise) are proportional to the total concentration of the dye, while the former is also proportional to the very small number of analyte particles and, therefore, the signal is dominated by the noise/background. Thus, even at the highest affinity of the recognition tag against the virus, an additional step is required to raise the signal-to-background ratio.

What is needed, therefore, is a rapid, accurate, and highly sensitive method and system for detecting low viral loads. It is to such a method and system that embodiments of the present invention are directed.

BRIEF SUMMARY OF THE INVENTION

As specified in the Background Section, there is a great need in the art to identify technologies for accurately and reliably detecting low viral loads and use this understanding to develop novel methods and systems for such detection. The present invention satisfies this and other needs. Embodiments of the present invention relate generally to methods and systems for early detection of viral diseases, and more specifically to systems and methods for early detection of viral diseases that are capable of detecting very low viral loads, such as for example and not limitation, SARS-CoV-2 loads.

In one aspect, the invention provides a system for detecting a low viral load in a subject infected with the virus, the system comprising:

a test device comprising an aqueous two-phase system (ATPS), a tagged protein/antibody/receptor/aptamer specific for the virus, and a magnetic particle operatively coupled to the protein/antibody/receptor/aptamer specific for the virus;

a permanent magnet providing a magnetic field; and an apparatus for visualizing the tagged protein/antibody/receptor/aptamer specifically bound to the viral particles, wherein a sample from the subject containing the virus is introduced into the test device, wherein the tagged protein/antibody/receptor/aptamer and the magnetic particle specifically bind to the virus in the test device to create a sandwich assembly, wherein the test device is shaken to emulsify the ATPS, wherein the test device is configured to allow separation of the ATPS into two different phases, wherein the test device has a region configured to interact with the visualization apparatus, and wherein the test device optionally has an hourglass shape.

In some embodiments, the ATPS is selected to promote partitioning of the emulsified ATPS in the presence of the magnetic field. In some embodiments, the ATPS comprises a water/organic system or a polymer/salt system.

In some embodiments, the tagged protein/antibody/receptor/aptamer comprises a fluorescent tag.

In some embodiments, the magnetic particle comprises spinel ferrites of the formula $MFe_2O_4$ where M=Co, Ni, Mn, or Fe.

In some embodiments, the test device is positioned within the magnetic field to promote partitioning of the emulsified ATPS in the presence of the magnetic field, such that the sandwich assembly migrates to the water phase and concentrates for visualization of the tag. In some embodiments, the characteristics of the magnetic field are optimized to promote partitioning of the emulsified ATPS in the presence of the magnetic field, such that the sandwich assembly migrates to the water phase and concentrates for visualization of the tag.

In some embodiments, unbound dye is located in a different phase of the ATPS than the sandwich assembly and is removed from the test device.

In some embodiments, the tagged protein/antibody/receptor/aptamer specifically bound to the viral particles is detected and/or quantified by the visualization apparatus.

In some embodiments, the sample is a biological fluid sample or a cell sample from the subject. In some embodiments, the sample is a saliva sample.

In some embodiments, the virus is SARS-CoV-2. In some embodiments, the protein/antibody/receptor/aptamer comprises ACE2, a monoclonal antibody specific for the Spike protein of SARS-CoV-2, and an aptamer specific for the Spike protein of SARS-CoV-2.

In another aspect, the invention provides a method for detecting viral particles in a subject having a low viral load, the method comprising:

obtaining a sample from the subject;

optionally preparing the sample;

introducing the sample into a test device, the test device comprising an aqueous two-phase system (ATPS), a tagged protein/antibody/receptor/aptamer specific for the virus, and a magnetic particle operatively coupled to the protein/antibody/receptor/aptamer specific for the virus;

shaking the test device to emulsify the ATPS;

positioning the test device in proximity to a permanent magnet providing a magnetic field; and visualizing the tagged protein/antibody/receptor/aptamer specifically bound to the viral particles with a visualization apparatus, wherein the tagged protein/antibody/receptor/aptamer and the magnetic particle specifically bind to the virus in the test device to create a sandwich assembly, wherein the test device is configured to allow separation of the ATPS into two different phases, wherein the test device has a region configured to interact with the visualization apparatus, and wherein the test device optionally has an hourglass shape.

In some embodiments, the ATPS is selected to promote partitioning of the emulsified ATPS in the presence of the magnetic field. In some embodiments, the ATPS comprises a water/organic system or a polymer/salt system.

In some embodiments, the tagged protein/antibody/receptor/aptamer comprises a fluorescent tag.

In some embodiments, the magnetic particle comprises spinel ferrites of the formula $MFe_2O_4$ where M=Co, Ni, Mn, or Fe.

In some embodiments, the test device is positioned within the magnetic field to promote partitioning of the emulsified ATPS in the presence of the magnetic field, such that the sandwich assembly migrates to the water phase and concentrates for visualization of the tag. In some embodiments, the characteristics of the magnetic field are optimized to promote partitioning of the emulsified ATPS in the presence of the magnetic field, such that the sandwich assembly migrates to the water phase and concentrates for visualization of the tag.

In some embodiments, unbound dye is located in a different phase of the ATPS than the sandwich assembly and is removed from the test device.

In some embodiments, the tagged protein/antibody/receptor/aptamer specifically bound to the viral particles is detected and/or quantified by the visualization apparatus.

In some embodiments, the sample is a biological fluid sample or a cell sample from the subject. In some embodiments, the sample is a saliva sample.

In some embodiments, the virus is SARS-CoV-2. In some embodiments, the protein/antibody/receptor/aptamer comprises ACE2, a monoclonal antibody specific for the Spike protein of SARS-CoV-2, and an aptamer specific for the Spike protein of SARS-CoV-2.

In another aspect, the invention provides a device for detecting viral particles in a subject having a low viral load, the test device comprising:

an aqueous two-phase system (ATPS);

a tagged protein/antibody/receptor/aptamer specific for the virus;

a magnetic particle operatively coupled to the protein/antibody/receptor/aptamer specific for the virus; and a portion configured to interact with a visualization apparatus to detect the tagged protein/antibody/receptor/aptamer specifically bound to the viral particles, wherein a sample from the subject containing the virus is introduced into the device, wherein the tagged protein/antibody/receptor/aptamer and the magnetic particle specifically bind to the virus in the device to create a sandwich assembly, wherein the device is shaken to emulsify the ATPS, wherein the device is configured to allow separation of the ATPS into two different phases, wherein the device is positioned in proximity to a permanent magnet providing a magnetic field and wherein the device optionally has an hourglass shape.

In some embodiments, the ATPS is selected to promote partitioning of the emulsified ATPS in the presence of the magnetic field. In some embodiments, the ATPS comprises a water/organic system or a polymer/salt system.

In some embodiments, the tagged protein/antibody/receptor/aptamer comprises a fluorescent tag.

In some embodiments, the magnetic particle comprises spinel ferrites of the formula $MFe_2O_4$ where M=Co, Ni, Mn, or Fe.

In some embodiments, the device is positioned within the magnetic field to promote partitioning of the emulsified ATPS in the presence of the magnetic field, such that the sandwich assembly migrates to the water phase and concentrates for visualization of the tag. In some embodiments, the characteristics of the magnetic field are optimized to promote partitioning of the emulsified ATPS in the presence of the magnetic field, such that the sandwich assembly migrates to the water phase and concentrates for visualization of the tag.

In some embodiments, unbound dye is located in a different phase of the ATPS than the sandwich assembly and is removed from the test device.

In some embodiments, the tagged protein/antibody/receptor/aptamer specifically bound to the viral particles is detected and/or quantified by the visualization apparatus.

In some embodiments, the sample is a biological fluid sample or a cell sample from the subject. In some embodiments, the sample is a saliva sample.

In some embodiments, the virus is SARS-CoV-2. In some embodiments, the protein/antibody/receptor/aptamer comprises ACE2, a monoclonal antibody specific for the Spike protein of SARS-CoV-2, and an aptamer specific for the Spike protein of SARS-CoV-2.

These and other objects, features and advantages of the present invention will become more apparent upon reading the following specification in conjunction with the accompanying description, claims and drawings.

BRIEF DESCRIPTION OF THE DRAWINGS

FIG. 1 *a*-1*n* represents a schematic of an embodiment of the invented system for detecting SARS-CoV-2. The invented system allows the analysis of respiratory samples in one step: (b) ATPS system of immiscible liquids (c), upon shaking, forms an emulsion (d), in which (f) the premixed components—fluorescent tag, mNPs (g-h) labeled with a recognition label—assemble (i-j) with SARS-CoV-2 virus (and not assemble w/o virus); (e) upon coalescence in magnetic field (k) the separation of labeled viral particles (1) and dye (m) happens along with the concentration in a specific small volume allowing (n) visualization of positive test result.

DETAILED DESCRIPTION OF THE INVENTION

As specified in the Background Section, there is a great need in the art to identify technologies for accurately and reliably detecting low viral loads and use this understanding to develop novel methods and systems for such detection. The present invention satisfies this and other needs. Embodiments of the present invention relate generally to methods and systems for early detection of viral diseases, and more specifically to systems and methods for early detection of viral diseases that are capable of detecting very low viral loads, such as for example and not limitation, SARS-CoV-2 loads.

To simplify and clarify explanation, the method and system is described below as a system for detecting low loads of SARS-CoV-2. One skilled in the art will recognize, however, that the invention is not so limited. The method and system can also be adapted for use in detection of low loads of any virus in any subject, provided that there are antibodies capable of specifically detecting that disease.

To facilitate an understanding of the principles and features of the various embodiments of the invention, various illustrative embodiments are explained below. Although exemplary embodiments of the invention are explained in detail, it is to be understood that other embodiments are contemplated. Accordingly, it is not intended that the invention is limited in its scope to the details of construction and arrangement of components set forth in the following description or examples. The invention is capable of other embodiments and of being practiced or carried out in various ways. Also, in describing the exemplary embodiments, specific terminology will be resorted to for the sake of clarity.

It must also be noted that, as used in the specification and the appended claims, the singular forms "a," "an" and "the" include plural references unless the context clearly dictates otherwise. For example, reference to a component is intended also to include composition of a plurality of components. References to a composition containing "a" constituent is intended to include other constituents in addition to the one named. In other words, the terms "a," "an," and "the" do not denote a limitation of quantity, but rather denote the presence of "at least one" of the referenced item.

As used herein, the term "and/or" may mean "and," it may mean "or," it may mean "exclusive-or," it may mean "one," it may mean "some, but not all," it may mean "neither," and/or it may mean "both." The term "or" is intended to mean an inclusive "or."

Also, in describing the exemplary embodiments, terminology will be resorted to for the sake of clarity. It is intended that each term contemplates its broadest meaning as understood by those skilled in the art and includes all technical equivalents which operate in a similar manner to accomplish a similar purpose. It is to be understood that embodiments of the disclosed technology may be practiced without these specific details. In other instances, well-known methods, structures, and techniques have not been shown in detail in order not to obscure an understanding of this description. References to "one embodiment," "an embodiment," "example embodiment," "some embodiments," "certain embodiments," "various embodiments," etc., indicate that the embodiment(s) of the disclosed technology so described may include a particular feature, structure, or characteristic, but not every embodiment necessarily includes the particular feature, structure, or characteristic. Further, repeated use of the phrase "in one embodiment" does not necessarily refer to the same embodiment, although it may.

As used herein, the term "about" should be construed to refer to both of the numbers specified as the endpoint (s) of any range. Any reference to a range should be considered as providing support for any subset within that range. Ranges may be expressed herein as from "about" or "approximately" or "substantially" one particular value and/or to "about" or "approximately" or "substantially" another particular value. When such a range is expressed, other exemplary embodiments include from the one particular value and/or to the other particular value. Further, the term "about" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

Throughout this description, various components may be identified having specific values or parameters, however, these items are provided as exemplary embodiments. Indeed, the exemplary embodiments do not limit the various aspects and concepts of the present invention as many comparable parameters, sizes, ranges, and/or values may be implemented. The terms "first," "second," and the like, "primary," "secondary," and the like, do not denote any order, quantity, or importance, but rather are used to distinguish one element from another.

It is noted that terms like "specifically," "preferably," "typically," "generally," and "often" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention. It is also noted that terms like "substantially" and "about" are utilized herein to represent the inherent degree of uncertainty that may be attributed to any quantitative comparison, value, measurement, or other representation.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "50 mm" is intended to mean "about 50 mm."

It is also to be understood that the mention of one or more method steps does not preclude the presence of additional method steps or intervening method steps between those steps expressly identified. Similarly, it is also to be understood that the mention of one or more components in a composition does not preclude the presence of additional components than those expressly identified.

Definitions

As used herein, the term "subject" or "patient" refers to mammals and includes, without limitation, human and veterinary animals. In a preferred embodiment, the subject is human.

A "disease" is a state of health of a subject wherein the subject cannot maintain homeostasis, and wherein if the disease is not ameliorated then the subject's health continues to deteriorate. In contrast, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health.

The terms "treat" or "treatment" of a state, disorder or condition include: (1) preventing or delaying the appearance of at least one clinical or sub-clinical symptom of the state, disorder or condition developing in a subject that may be afflicted with or predisposed to the state, disorder or condition but does not yet experience or display clinical or subclinical symptoms of the state, disorder or condition; or (2) inhibiting the state, disorder or condition, i.e., arresting, reducing or delaying the development of the disease or a relapse thereof (in case of maintenance treatment) or at least one clinical or sub-clinical symptom thereof; or (3) relieving the disease, i.e., causing regression of the state, disorder or condition or at least one of its clinical or sub-clinical symptoms. The benefit to a subject to be treated is either statistically significant or at least perceptible to the patient or to the physician.

The term "antibody," as used herein, refers to an immunoglobulin molecule which specifically binds with an antigen. An antibody can be an intact immunoglobulin derived from a natural source or from a recombinant source. Such antibody can comprise an immunoreactive portion of an intact immunoglobulin. The antibody may exist in a variety of forms including, for example, polyclonal antibodies, monoclonal antibodies, Fv, Fab and F(ab)2, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antigen" or "Ag" as used herein is defined as a molecule that provokes an immune response. This immune response may involve either antibody production, or the activation of specific immunologically-competent cells, or both. Any macromolecule, including virtually all proteins or peptides, can serve as an antigen. Furthermore, antigens can be derived from recombinant or genomic DNA. Any DNA which comprises a nucleotide sequences or a partial nucleotide sequence encoding a protein that elicits an immune response therefore encodes an "antigen" as that term is used herein. Furthermore, an antigen need not be encoded solely by a full-length nucleotide sequence of a gene. Partial nucleotide sequences of more than one gene may be used, for example these nucleotide sequences may be arranged in various combinations to elicit a desired immune response. Moreover, an antigen need not be encoded by a "gene" at all. An antigen can be generated synthesized or can be derived from a biological sample.

The term "binding" refers to a direct association between at least two molecules, due to, for example, covalent, electrostatic, hydrophobic, ionic and/or hydrogen-bond interactions.

"Contacting" refers to a process in which two or more molecules or two or more components of the same molecule or different molecules are brought into physical proximity such that they are able undergo an interaction. Molecules or components thereof may be contacted by combining two or more different components containing molecules, for example by mixing two or more solution components, preparing a solution comprising two or more molecules such as target, candidate or competitive binding reference molecules, and/or combining two or more flowing components.

In the context of the field of medicine, the term "prevent" encompasses any activity which reduces the burden of mortality or morbidity from disease. Prevention can occur at primary, secondary and tertiary prevention levels. While primary prevention avoids the development of a disease, secondary and tertiary levels of prevention encompass activities aimed at preventing the progression of a disease and the emergence of symptoms as well as reducing the negative impact of an already established disease by restoring function and reducing disease-related complications.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally.

Methods and Systems of the Invention

As discussed herein, a problem with conventional testing methods and systems for early detection of viral diseases (i.e., in stages with low viral loads) is the ability to concentrate the viral particles for accurate detection. Briefly, the invented methods and systems use a known protein/receptor/antibody (e.g., ACE2) in one-step express test technology for detecting a living virus, e.g., SARS-CoV-2. The technology is designed to be cost-efficient to produce rapid test systems for the personal use/POC. Additionally, in the invented method and system, the viral sample is kept intact (in contrast to majority of test methods that rely on lysis). The invention combines robust separation techniques, already proved to work with viral particles, a stable optical visualization protocol via a "sandwich" functionalization of a living virus, and a special design of the rapid test system, fabricated using advanced manufacturing technology. The sample to be tested can be obtained from a biological fluid from a subject, such as for example and not limitation, saliva, blood, plasma, sputum, nasal secretions, cerebrospinal fluid, mucus, and the like. Alternatively, the sample to be tested can comprise cells from a subject, such as for example and not limitation, skin cells, cells obtained from the nose, nasopharyngeal cavities, or sinus cavities; buccal cells, throat cells, and the like.

Among simple methods, fluorescent tag visualization is attractive as it allows detection of the analyte in a single step. However, in order to reach the aim of detection of viral particles in a liquid sample at extremely low concentration the typical fluorescent signal is too weak to detect without special tools. This suggests a major barrier for such an early detection technology: both the efficiency of binding of a tag/beacon to the analyte (~signal) and the background fluorescence (~noise) are proportional to the total concentration of the dye, while the former is also proportional to the very small number of analyte particles and, therefore, the signal is dominated by the noise/background. Thus, even at the highest affinity of the recognition tag against the virus, an additional step can be required to raise the signal-to-background ratio. The invented system and method address this problem among others. The invented approach combines in one step (a) removal of the free fluorescent tag from the sensing volume, and (b) concentration of the labeled viral particles in this volume. These steps can be achieved by conjugating the known protein/receptor/antibody to both a fluorescent tag (for visualization) and to a magnetic nanoparticle (to aid in concentration) in combination with an aqueous two-phase separation (ATPS) system. The use of the ATPS system can enable the separation and concentration of the viral particles, assembled with the fluorescent tags and mNPs, in a small detection volume. The ATPS system and reagents can be in a test device. Since the free dye should be completely separated from such a detection volume, the background fluorescence can be eliminated, leaving only the signal due to viral assemblies. Optimization of the ATPS liquids should allow the inventors to separate the particles of interest. The specific mechanisms for droplet formation, transport and coalescence, and their dependence on the hydration properties of components (mNP, fluorescent tag, viral particles, sandwich assemblies) can be studied to identify their role in accelerating the viral assembling and partitioning. The ATPS liquid can emulsified by shaking the test device and, upon coalescence in the magnetic field from permanent magnet(s), the separation and concentration of the viral particles, assembled with the fluorescent tags and mNPs, can happen in a small detection volume. Since the free dye should be completely separated from such a detection volume, the background fluorescence should be eliminated, leaving only the signal due to viral assemblies. Specifically, ATPS creates, when emulsified, a large (transient) surface area and confines the viral particles and other biochemical components within a microscopic volume of an individual micro-droplet (FIG. 1*d*). Greatly enhanced surface effects, turbulent flows created during emulsification, transport of chemicals inside the droplets towards desired location—all these physical/chemical phenomena should improve the yield of the binding reaction to be investigated (a simple solution of reaction rate equation is shown in FIG. 1*j* to illustrate the expected effect). At the same time, upon liquid phase coalescence—given the proper choice of the hydrophilicity of the liquid phases—the viral particles and free dye molecules can be separated in different ATPS phases.

The concentration of particles should happen under the gradient of a magnetic field which can be applied by placing a Neodymium permanent magnet in the frame of the invented system and in the vicinity of the test device. In the viral "sandwich" assembly, multiple mNPs (e.g., small size <16 nm paramagnetic particles to prevent magnetic agglomeration) should bind to a single virus. Thus, the inventors expect that the magnetic drag force will be sufficient to transport the assembly within the solution volume and across the phase interface as needed. The test system can be designed together with a frame where the magnet is placed, with a magnetic field computed to draw most efficiently the mNP to desired location. One possible solution is to bring all viral assemblies to the interface between the liquid phases. Thus, all assemblies can be concentrated within a small volume, floating in the bottleneck at the phase boundary. For a potentially optimal design of the test system, the background fluorescence of residual dye should be weaker than of the concentrated virus, meaning that the ratio of the volume of the test chamber and of the bottleneck focal point should be kept small (of the order of 1:1000). Should this two-dimensional concentration be insufficient, the viral assemblies can be manipulated to pass the ATPS interface and concentrate next to the magnet, in the volume thermodynamically prohibited for the free dye molecules (by appropriate choice of the solvent liquid). The chosen method of concentration, e.g., a combination of hydration and magnetic force, should allow the inventors to efficiently separate the free tag and tagged virus within a wide range of their materials properties (hydration, density and size).

Examplary Embodiment

The following is an exemplary embodiment of the claimed method and system designed to detect SARS-CoV-2; however, the principles described herein can be applied to any viral disease.

For the mechanism for detection of viral particles the inventors chose a fluorescent probe, labeled with the recognition label (RecLa), which has high affinity to a specific glycoprotein of SARS-CoV-2. In order to ensure specificity of tagging, the inventors can use natural/wild RecLa—angiotensin I converting enzyme 2 (ACE-2), known to bind to the spike (S) glycoprotein from the SARS-CoV-2 coronavirus. Alternatively, a modified mACE-2 (protein engineered RecLa), with a higher affinity and stability compared to wild ACE-2 can be used in the methods and systems of the invention. Should even higher affinity (lower dissociation constants) be required to reach the target LoD, a customized monoclonal antibody (mAb) can be developed against S-protein. Alternatively, existing or developing new aptamers to S protein may be utilized in the invented methods and systems. Also, nanometer scale magnetic particles (mNP) can be functionalized with ACE-2 (or the alternatives discussed above) to recognize the virus, thus forming with the dye molecules a sandwich structure as shown in FIG. 1*j*. Due to high specificity of RecLa, both the dye and the mNP can assemble only at the surface of the virus. A magnetic field can be used to concentrate the mNP and the viral assemblies into the specific detection volume. Non-assembled mNPs should give no background signal. Non-assembled dye molecules can be excluded from the detection volume where the virus is concentrated. In this way, the invented systems and methods can achieve highly specific binding and ultimately a test system with low rates of false negatives, even at very small LoD values of the order of 1,000 particles/sample.

In the invented methods and systems, the original liquid sample, containing a very small number of viral particles ($10^3$-$10^4$ pc. for presymptomatic patients), can be added to an aqueous two-phase separation (ATPS) system, along with a premix of reagents (fluorescent tag and mNP functionalized with ACE-2, the protein recognized by the SARS-CoV-2 virus) in a test system. ATPS is emulsified by shaking the test system and, upon coalescence in the magnetic field from permanent magnet(s), the separation and concentration of the viral particles, assembled with the tags and mNPs, can happen in a small detection volume. Since the free dye should be completely separated from such a detection volume, the background fluorescence will be eliminated, leaving only the signal due to viral assemblies. The ATPS system and reagents can be present in a test device.

At low viral load, the process of tagging the virus with mNPs and dye may need facilitation. For that purpose, and also to enhance the separation of free dye (background) from the functionalized assemblies (signal), the ATPS technology can be implemented. A system of two immiscible liquids (FIG. 1*b*, 1*c*), specifically: either polymer/salt or water/organic solvent ATPS, can be carefully selected. ATPS creates, when emulsified, a large (transient) surface area and confines the viral particles and other biochemical components within a microscopic volume of an individual microdroplet (FIG. 1*d*). Greatly enhanced surface effects, turbulent flows created during emulsification, transport of chemicals inside the droplets towards desired location—all these physical/chemical phenomena should improve the yield of the binding reaction to be investigated (a simple solution of reaction rate equation is shown in FIG. 1*j* to illustrate the expected effect). At the same time, upon liquid phase coalescence—given the proper choice of the hydrophilicity of the liquid phases—the viral particles and free dye molecules can be separated in different ATPS phases. This technology has been successfully used for both inorganic particles, organic macromolecules and, most importantly, viral particles. A large spectrum of ATPS liquids should allow the inventors to separate the particles of interest. The specific mechanisms for droplet formation, transport and coalescence, and their dependence on the hydration properties of components (mNP, beacon, viral particles, assemblies) can be studied to identify their role in accelerating the viral assembling and partitioning.

The concentration of particles should happen under the gradient of a magnetic field which can be applied by placing a Neodymium permanent magnet in the frame of the invented system and in the vicinity of the test device. In the viral "sandwich" assembly, multiple mNPs (e.g., small size <16 nm paramagnetic particles to prevent magnetic agglomeration) should bind to a single virus. Thus, the inventors expect that the magnetic drag force will be sufficient to transport the assembly within the solution volume and across the phase interface as needed. In the initial experiments, the amount of field required to manipulate the paramagnetic particles themselves (spinel ferrites $MFe_2O_4$ where M=Co, Ni, Mn, or Fe) will be studied. The inventors can experiment with the size of the particles to ensure optimum manipulation at no agglomeration and clogging the system.

The test system can be designed together with a frame where the magnet is placed, with a magnetic field computed to draw most efficiently the mNP to desired location. One possible solution is to bring all viral assemblies to the interface between the liquid phases. Thus, all assemblies will be concentrated within a small volume, floating in the bottleneck at the phase boundary (FIG. 1*e*, 1*m*). For a potentially optimal design of the test system, the background fluorescence of residual dye should be weaker than of the concentrated virus, meaning that the ratio of the volume of the test chamber and of the bottleneck focal point should be kept small (of the order of 1:1000). Should this two-dimensional concentration be insufficient, the viral assemblies can be manipulated to pass the ATPS interface and concentrate next to the magnet, in the volume thermodynamically prohibited for the free dye molecules (by appropriate choice of the solvent liquid). Chosen method of concentration—combination of hydration and magnetic force—should allow the inventors to efficiently separate the free tag and tagged virus within a wide range of their materials properties (hydration, density and size).

This system and method can allow the use of the same sample for post-screening analysis, since the envelop of the virus is kept intact and, upon standard lysing, the nucleic acid can be released.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1: Development of the ATPS System

Liquid two-phase systems in the form of either polymer/salt aqueous two-phase system or water/immiscible organic solvent system have been widely used in biotechnology for purification of components ranging from small molecules to cells, for the separation of biomacromolecules and natural products. While a large spectrum of ATPS liquids should allow the inventors to separate the particles of interest, specific mechanisms for droplet formation, transport and coalescence will be studied to identify their role in accelerating the viral assembling. Although the concentration of virus in the volume of the invented system is "non-measurable", the concentration gets much higher within a single micro-droplet, inversely proportional to the droplet volume. In this Example, the inventors will investigate the kinetics of the chemical reactions, the role of the microscale flow and surface effects. The following hypotheses will be tested: 1. Proper selection of the components of the ATPS will lead to most efficient separation of the viral assemblies from the non-bound dye molecules. 2. For different ATPS components, the combination of hydration forces, magnetic field drag, microscale flows, viscosity and surface effects should have an optimum to maximize the yield of binding reaction, separation and concentration of viral particles. 3. For a given ATPS system there is expected to be an optimal design of the shape/form factor for the invented system, which will optimize configuration of magnetic field for the best concentration and visualization of labeled virus and achieve the lowest LoD. 4. Doping of the iron oxide superparamagnetic material results in increase of mNP magnetic susceptibility and magnetization, making magnetic drag/concentration faster and more efficient. 5. Diels-Alder linkage and tetrafluorophenyl ester reaction will produce stable linkers for both mNP and dye to the RecLa protein.

The SARS-Cov-2 reporter will be conjugated to an inexpensive high quantum yield dye, such as Fluorescein or Rhodamine, labeled by ACE-2 RecLa using a well-described tetrafluorophenyl ester reaction to attack the primary amines, thereby limiting the potential for disrupting the SARS-Cov-2 binding site. Should a stability of the dye luminescence be improved, a series of Alexa chromophores can be used.

For functionalization of mNPs, the inventors will leverage the previously described methods for magnetic nanoparticle synthesis using the previously described Diels-Alder linkage chemistry for surface modification. The inventors will adapt this technique to attach the RecLa to the surface of mNP (FIG. 1*f*). The inventors will explore doping iron oxide with Co, Ni, Mn, or Fe, creating different spinel ferrites, to determine the influence of the composition on the magnitude and stability of magnetic susceptibility. Preliminary results indicate cobalt doping of the iron oxide increases the mass magnetization significantly without impacting the crystal structure or increasing the particle size (7-12 nm) (FIG. 1*g*). The stability as a function of dopant will be determined through accelerated aging studies in simulated storage conditions. Every month samples will be selected to determine the loss of magnetization via SQUID magnetometry, correlated with oxidation as determined by X-Ray Diffraction. The crystallinity of the mNPs allows for a conserved surface chemistry to be used to functionalize it regardless of dopant composition.

The inventors will explore a range of ATPS systems, making sure that neither water nor organic phase may disrupt lipid membranes of SARS-CoV-2, leading to disintegration of assemblies. This potential problem can be mitigated by choosing proper organic phase from a large range of choices to minimize its interactions with the virus membrane. The inventors will begin with a PEG/dextrane system. Alternatively, polymer/salt ATPS systems can be used, that are much more biocompatible than a water/organic system. The selection of the ATPS system is important for ensuring that the viral envelope is not disrupted so that further diagnostic testing, e.g., PCR, can be performed on the viral particles concentrated by this method.

The inventors will study the fluid transport, both experimentally and theoretically. The detailed reaction rate calculations will be performed as needed, using COMSOL and home-written codes. Experiments will be performed to eliminate potential aggregation/clustering of mNPs. For calibration purposes, the inventors will perform fluorescence measurements of labeled bio-functionalized mNPs with/without virus, determine the level of background of the free dye molecules and measure the sensitivity of the invented system via taking the fluorescent signal at the lowest concentrations with/without optical instrumentation. These experiments will be performed with either viral-like particles or fully inactivated virus first.

At a later stage of the project, the inventors will perform integration of all components of the test platform. Given the steps of optimization of the ATPS separation are achieved, specifically that (i) the sandwich assemblies should reside in the desired ATPS phase and (ii) that the paramagnetic mNP manipulation shows robust transport and concentration of the sandwich assemblies in a magnetic field, the inventors will build the prototype test devices. The shape, volume, geometry of frame, position of the Neodymium permanent magnet, shape of the concentrator/visualization volume and other factors will be optimized at this stage.

The sandwich assembly structure dye:RecLa/virus/RecLa:mNP should have a different partition function (related to its hydration properties) than the free dye:RecLa and free mNP:RecLa, thus making the case for the ATPS separation. In addition, the shape of magnetic field will be designed to localize the viral assemblies in the detection volume. Potential design solutions include: localization of all viral particles at the flat interface between two aqueous phases within a zone with a narrow width; or localization of viral particles in a small nozzle, deep inside the phase non-accessible by free dye. To achieve the desired performance and keep the device cost low, a simple system of magnets should be designed. Should the magnetic manipulation require additional concentration, electric fields (collinear for increasing the drag force, or cross-directed for an extra spatial confinement) will be applied via a system of electrodes.

For practical application of the invented system, collecting the saliva sample and dissolving it will follow standard protocols. The original liquid sample, containing—for pre-symptomatic patients—a very small number of viral particles ($10^3$-$10^4$ pc.) will be added to aqueous phase of ATPS system (FIG. 1*a*). The test system, filled with premix of reagents and second ATPS (less hydrophilic phase) will be shaken thoroughly to produce an emulsion (FIG. 1*d*). Next, for coalescence, the test will be inserted in the frame containing permanent magnet(s). Magnetic field and ATPS assisted separation and concentration should result in collecting all viral particles, assembled with the multiple (ca. 100) dye molecules (and mNP), in a small detection volume. Specific design of this volume will be determined in the course of the Example. Since the free dye will be completely separated from the detection volume, we expect the fluorescence should be seen by eye, or, alternatively, can be taken by the smartphone camera for more quantitative analysis.

The inventors will test analytical and diagnostic sensitivity of the prototype device on model Hcov-NL63 and real SARS-CoV-2 virus, determining the test accuracy against standard PCR.

While several possible embodiments are disclosed above, embodiments of the present invention are not so limited. These exemplary embodiments are not intended to be exhaustive or to unnecessarily limit the scope of the invention, but instead were chosen and described in order to explain the principles of the present invention so that others skilled in the art may practice the invention. Indeed, various modifications of the invention in addition to those described herein will become apparent to those skilled in the art from the foregoing description. Such modifications are intended to fall within the scope of the appended claims.

What is claimed is:

1. A system for detecting a low viral load comprising $10^3$-$10^4$ viral particles/μL comprising SARS-COV-2 viral particles in a presymptomatic subject infected with SARS-COV-2 virus, the system comprising:

a test device comprising an aqueous two-phase system (ATPS), a tagged protein/antibody/receptor/aptamer specific for the virus, and a magnetic particle operatively coupled to the protein/antibody/receptor/aptamer specific for the virus;

a permanent magnet providing a magnetic field; and an apparatus for visualizing the tagged protein/antibody/receptor/aptamer specifically bound to the viral particles, wherein the test device is configured to introduce a sample from the subject containing the virus, wherein the tagged protein/antibody/receptor/aptamer and the magnetic particle are capable to specifically bind to the virus in the test device to create a sandwich assembly, wherein the test device is capable of being shaken to emulsify the ATPS, wherein the test device is configured to allow separation of the ATPS into two different phases, wherein upon separation the tagged protein/antibody/receptor/aptamer that does not bind to the virus is located in a different phase of the ATPS than the sandwich assembly, wherein the test device has a region comprising a detection volume configured to interact with the visualization apparatus and the detection volume comprises the sandwich assembly but does not comprise the tagged protein/antibody/receptor/aptamer not binding to the virus or free tags, wherein the tagged protein/antibody/receptor/aptamer comprises a monoclonal antibody comprising angiotensin I converting enzyme 2 (ACE2), and wherein the magnetic particle is operatively coupled to the protein/antibody/receptor/aptamer by a linker below formed via Diels-Alder linkage reaction:

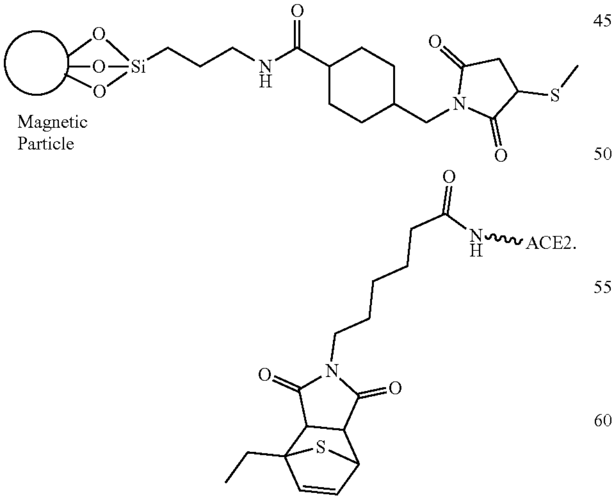

2. The system of claim 1, wherein the ATPS is selected to promote partitioning of the emulsified ATPS in the presence of the magnetic field.

3. The system of claim 1, wherein the ATPS comprises a water/organic system or a polymer/salt system.

4. The system of claim 1, wherein the tagged protein/antibody/receptor/aptamer comprises a fluorescent tag.

5. The system of claim 1, wherein the magnetic particle comprises spinel ferrites of the formula $MFe_2O_4$ where M=Co, Ni, Mn, or Fe.

6. The system of claim 1, wherein the test device is positioned within the magnetic field to promote partitioning of the emulsified ATPS in the presence of the magnetic field, such that the sandwich assembly migrates to the water phase and concentrates for visualization of the tag.

7. The system of claim 1, wherein the characteristics of the magnetic field are optimized to promote partitioning of the emulsified ATPS in the presence of the magnetic field, such that the sandwich assembly migrates to the water phase and concentrates for visualization of the tag.

8. The system of claim 1, wherein the system is further configured to remove the tagged protein/antibody/receptor/aptamer that does not bind to the virus from the test device.

9. The system of claim 1, wherein the tagged protein/antibody/receptor/aptamer specifically bound to the viral particles is detected and/or quantified by the visualization apparatus.

10. The system of claim 1, wherein the sample is a biological fluid sample or a cell sample from the subject.

11. A device for detecting viral particles comprising SARS-COV-2 viral particles in a presymptomatic subject having a low viral load comprising $10^3$-$10^4$ viral particles/μL, the device comprising:

an aqueous two-phase system (ATPS);

a tagged protein/antibody/receptor/aptamer specific for the virus;

a magnetic particle operatively coupled to the protein/antibody/receptor/aptamer specific for the virus; and a portion configured to interact with a visualization apparatus to detect the tagged protein/antibody/receptor/aptamer specifically bound to the viral particles, wherein the device is configured to introduce a sample from the subject containing the virus, wherein the tagged protein/antibody/receptor/aptamer and the magnetic particle are capable to specifically bind to the virus in the device to create a sandwich assembly, wherein the device is capable of being shaken to emulsify the ATPS, wherein the device is configured to allow separation of the ATPS into two different phases, wherein upon separation the tagged protein/antibody/receptor/aptamer that does not bind to the virus is located in a different phase of the ATPS than the sandwich assembly, wherein the device has a region comprising a detection volume in the portion configured to interact with the visualization apparatus and the detection volume comprises the sandwich assembly but does not comprise the tagged protein/antibody/receptor/aptamer not binding to the virus or free tags, wherein the device is positioned in proximity to a permanent magnet providing a magnetic field, and wherein the tagged protein/antibody/receptor/aptamer comprises a monoclonal antibody comprising angiotensin I converting enzyme 2 (ACE2), and wherein the magnetic particle is operatively coupled to the protein/antibody/receptor/aptamer by a linker below formed via Diels-Alder linkage reaction:

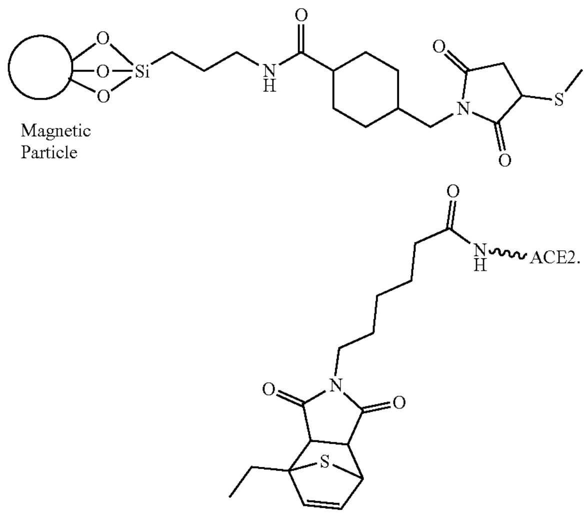

12. The device of claim 11, wherein the ATPS is selected to promote partitioning of the emulsified ATPS in the presence of the magnetic field.

13. The device of claim 11, wherein the magnetic particle comprises spinel ferrites of the formula $MFe_2O_4$ where M=Co, Ni, Mn, or Fe.

14. The device of claim 11, wherein the device is positioned within the magnetic field to promote partitioning of the emulsified ATPS in the presence of the magnetic field, such that the sandwich assembly migrates to the water phase and concentrates for visualization of the tag.

15. The device of claim 11, wherein the characteristics of the magnetic field are optimized to promote partitioning of the emulsified ATPS in the presence of the magnetic field, such that the sandwich assembly migrates to the water phase and concentrates for visualization of the tag.

16. The device of claim 11, wherein the device is further configured to remove the tagged protein/antibody/receptor/aptamer that does not bind to the virus.

17. The device of claim 11, wherein the tagged protein/antibody/receptor/aptamer specifically bound to the viral particles is detected and/or quantified by the visualization apparatus.

* * * * *